(12) United States Patent
Kavounas

(10) Patent No.: US 6,948,592 B2
(45) Date of Patent: Sep. 27, 2005

(54) ELEVATORS EQUIPPED WITH EMERGENCY MEDICAL DEVICES

(75) Inventor: Gregory T. Kavounas, Kirkland, WA (US)

(73) Assignee: Medtronic Emergency Response Systems, Inc., Redmond, WA (US)

(*) Notice: Subject to any disclaimer, the term of this patent is extended or adjusted under 35 U.S.C. 154(b) by 161 days.

(21) Appl. No.: 10/395,715

(22) Filed: Mar. 20, 2003

(65) Prior Publication Data

US 2004/0055828 A1 Mar. 25, 2004

Related U.S. Application Data

(60) Provisional application No. 60/413,264, filed on Sep. 23, 2002.

(51) Int. Cl.$^7$ .................................................. B66B 1/20
(52) U.S. Cl. ........................ 187/384; 187/388; 187/901
(58) Field of Search ................................ 187/401, 313, 187/239, 249, 380, 901, 381, 384, 388, 414, 391, 392

(56) References Cited

U.S. PATENT DOCUMENTS

| | | | | |
|---|---|---|---|---|
| 4,042,066 A | * | 8/1977 | Noone | 182/142 |
| 4,375,637 A | * | 3/1983 | Desjardins | 340/517 |
| 4,469,198 A | * | 9/1984 | Crump | 182/141 |
| 4,482,032 A | * | 11/1984 | Enriquez et al. | 187/392 |
| 4,619,265 A | | 10/1986 | Morgan et al. | |
| 5,080,199 A | * | 1/1992 | McCallum, III | 187/413 |
| 5,227,776 A | * | 7/1993 | Starefoss | 340/825.36 |
| 5,319,812 A | * | 6/1994 | Hanrahan et al. | 4/663 |
| 5,593,426 A | | 1/1997 | Morgan et al. | |
| 5,655,625 A | * | 8/1997 | Barker et al. | 187/249 |
| 6,000,505 A | * | 12/1999 | Allen | 187/391 |

FOREIGN PATENT DOCUMENTS

| | | |
|---|---|---|
| CN | 1154338 A | 7/1997 |
| DE | 197 51 024 A1 | 5/1999 |
| EP | 0 776 856 A2 | 6/1997 |
| JP | 11178800 | 7/1999 |
| SU | 1220673 A | 3/1986 |

OTHER PUBLICATIONS

"Managing an AED Program", Building Owners and Managers Association (BOMA) International and The American Heart Association (AHA), Jan. 2003.

International Preliminary Examination Report from corresponding International Application No. PCT/US03/29579 mailed Dec. 28, 2004 (5 pages).

* cited by examiner

*Primary Examiner*—Jonathan Salata
(74) *Attorney, Agent, or Firm*—Shumaker & Sieffert, P.A.

(57) ABSTRACT

The invention provides an elevator cab equipped with an emergency medical device, such as an automated external defibrillator (AED). The elevator cab equipped with the emergency medical device may be controlled in order to deliver the emergency medical device to a floor of a building on which an emergency medical situation occurred. In response to emergency medical input identifying the emergency medical situation, an elevator control unit overrides regular operation of the elevator cab in response to receiving emergency medical input, and directs the elevator cab to a floor on which an emergency medical situation occurs. For example, the elevator control unit may cancel active floor calls made by passengers within the elevator cab or individuals on one or more floors of the building and direct the elevator cab to the floor of the emergency situation.

69 Claims, 11 Drawing Sheets

ELEVATORS EQUIPPED WITH EMERGENCY MEDICAL DEVICES

This application claims priority from U.S. Provisional Application Ser. No. 60/413,264, filed Sep. 23, 2002, the entire content of which is incorporated herein by reference.

TECHNICAL FIELD

The invention relates to elevator cabs that are equipped with medical devices and their operation.

BACKGROUND

Cardiac arrest is a life-threatening medical condition that may be treated with external defibrillation. External defibrillation includes applying electrodes to a patient's chest and delivering an electric shock to the patient to depolarize the patient's heart and restore normal sinus rhythm. The chances that a patient's heart can be successfully defibrillated increase significantly if a defibrillation pulse is applied quickly.

In some cases, the patient's need is urgent and the patient cannot wait for trained personnel, such as paramedics, emergency medical technicians, or others trained in defibrillations techniques, to arrive. In recognition of the need for prompt treatment and the advantages of early defibrillation, automated external defibrillators (AEDs) are becoming more commonplace, and are available in venues such as airports, health clubs and auditoriums.

When an AED is used to treat a patient, much of the treatment is performed by the AED rather than the person who operates the AED. In general, the AED automatically measures the patient's cardiac signals, assesses whether a shock is indicated and charges a storage element in preparation for giving the shock. When a shock is indicated, the AED may cue the operator to administer the shock, or the AED may administer the shock automatically. In addition, many AEDs include visual displays, voice instructions and other audible messages that tell the operator about the status of the defibrillator. By delivering therapy in advance of arrival of emergency personnel, an AED can save a patient's life.

SUMMARY

In general, the invention is directed to an elevator cab equipped with an emergency medical device. The elevator cab equipped with the emergency medical device may be controlled in order to deliver the emergency medical device to a floor of a building on which an emergency medical situation occurred. Hence, the invention provides buildings with elevator cabs that have emergency medical devices therein. Furthermore, the invention provides device software and methods for controlling such elevators.

In accordance with the invention, an elevator system within a building includes an elevator cab that houses an emergency medical device, and optionally also an elevator control unit to control operation of the elevator cab. The emergency medical device may be any medical device, such as an automated external defibrillator (AED). The elevator cab may include a station to house the emergency medical device. The station may be mounted on or recessed within a wall of the elevator cab. For example, the station may be at least in part between a main vertical surface of a front panel of the elevator cab and a return of the front panel into which an elevator door recedes upon opening.

The elevator system responds to emergency medical input by directing the elevator cab equipped with the AED to a floor of an emergency medical situation. Initially, the elevator control unit receives emergency medical input signifying an emergency medical situation. The elevator control unit may receive the emergency medical input via a user input medium such as a switch or button. For example, the user may actuate a button associated with AED operation of the elevator cab on push button panel located on a floor of the building. The input may specify, for example, a floor on which the emergency medical situation occurred.

The elevator control unit overrides regular operation of the elevator cab in response to the input signifying an emergency medical situation. The elevator control unit may, for example, cancel active floor calls made by passengers within the elevator cab or individuals on one or more floors of the building. Further, if the elevator cab is part of a group of elevator cabs with dedicated floors to service, the elevator control unit may reconfigure operation of other elevator cabs within the group in order to service the floors no longer serviced by the elevator cab equipped with the AED.

In addition, the elevator system may initiate contact with a safety agency in response to the input signifying the emergency medical situation. For example, the elevator control unit may send an advisory to a safety agency to request that emergency personnel be dispatched to the scene of the emergency medical. The communication to the safety agency may include location information, as well as other pertinent information.

Further, the elevator control unit may convey information to passengers within the elevator cab in response to the input signifying an emergency medical situation. For instance, the elevator control unit may convey information to the passengers within the elevator cab apprising the passengers of the current situation.

The elevator control unit then directs the elevator cab to the floor on which the emergency medical situation occurred. However, the elevator control unit may direct the elevator cab to a floor on which a person trained to use the AED is located before directing the elevator cab to the floor of the emergency medical situation.

In one embodiment, the invention provides a method comprising receiving emergency medical input signifying an emergency medical situation at a floor of a building, overriding regular operation of an elevator cab that carries an emergency medical device in response to receiving the input and directing the elevator cab to the floor.

In another embodiment, the invention provides a system comprising an elevator cab moveable within a building, a traveling cable attached to the bottom of the cab and to a fixed point of the building, and a defibrillator in a station of the cab that communicates via the traveling cable.

In another embodiment, the invention provides a system comprising an enclosure with an openable elevator door, a front panel behind which the door recedes for opening, and a defibrillator in a station, wherein the station is at least in part between a main vertical surface of the front panel and the door when receded.

In a further embodiment, the invention provides a system comprising an elevator cab in a building, a station within the elevator cab that houses an emergency medical device, and an elevator control unit to control the operation of the elevator cab, the elevator control unit receiving input identifying an emergency situation, overriding regular operation of the elevator cab, and directing the elevator cab to a floor of the building on which the emergency situation occurs in response to the received input.

In another embodiment, the invention is directed to a computer-readable medium containing instructions cause a processor to receive a emergency medical input signifying a emergency medical situation, override regular operation of an elevator cab that carries an emergency medical device suitable for the situation in response to receiving the input, and direct the elevator cab to a floor on which the emergency situation occurs.

The invention may provide a number of advantages. In general, the techniques of the invention reduce the amount of time before an individual suffering an emergency medical situation, such as a sudden cardiac arrest, receives therapy in advance of arrival of emergency personnel. In some cases, this early therapy may save the life of the individual. In addition, the invention becomes standardized, i.e., people will know where an AED is within a building and how to summon the AED. Further, contacting a safety agency in response to receiving emergency medical input identifying the emergency medical situation advantageously reduces the amount of time before delivery of early advanced care to the patient. Also, the current infrastructure of the elevator control unit and traveling cables may be used for communication between the emergency medical device stationed within the elevator cab and either the elevator control unit or an emergency medical device control unit. Accordingly, there is no need for separate wiring to support the incorporation of an emergency medical device in the elevator cab, or to control travel of the elevator cab in response to a medical emergency.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
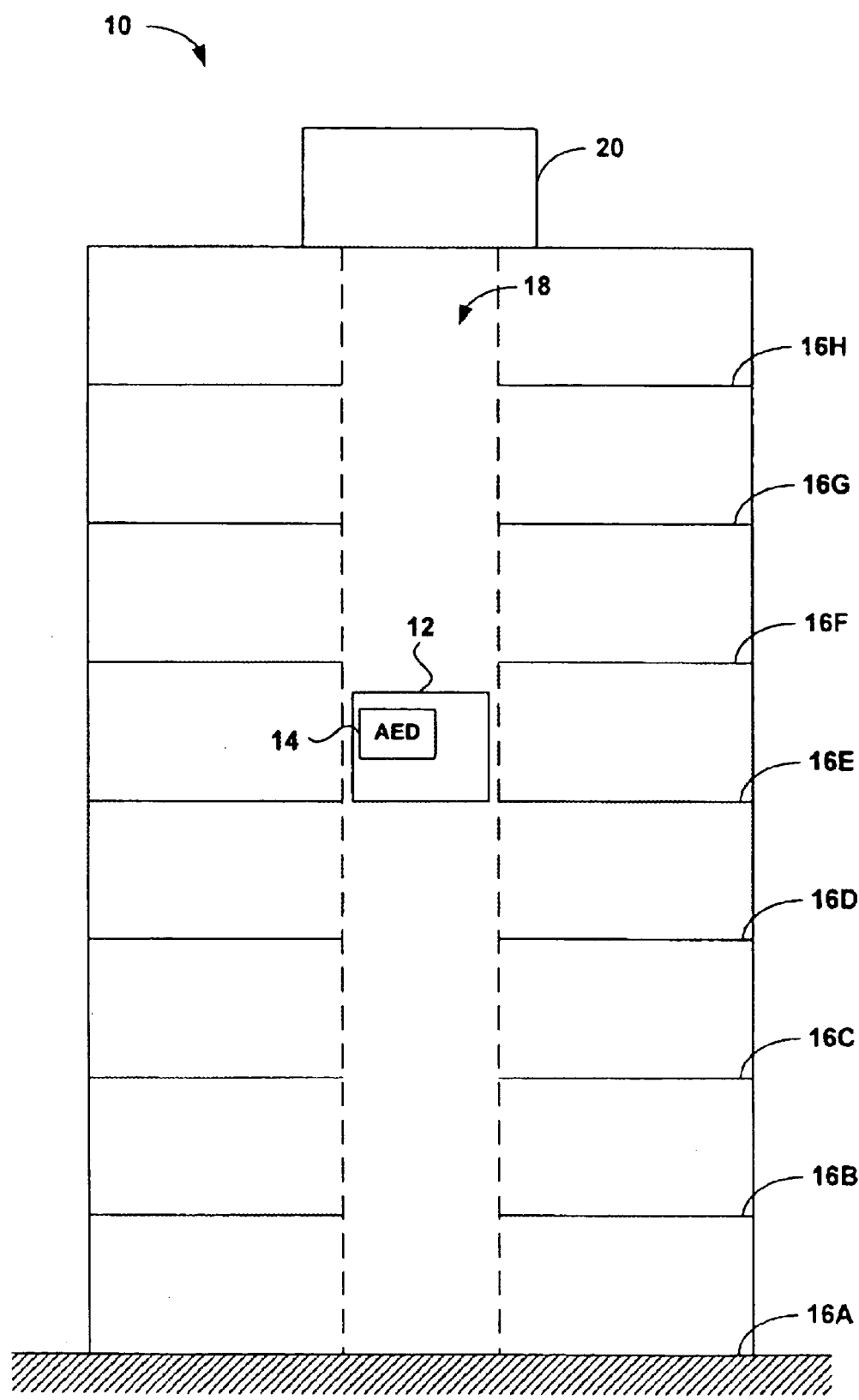
FIG. 1 is a diagram illustrating a building that includes an elevator cab equipped with an emergency medical device.

FIG. 1 is a diagram illustrating a building 10 that includes an elevator cab 12 equipped with an emergency medical device. A wide array of medical devices may be included, such as defibrillators, first aid kits or the like. For the sake of example, the invention will be described in context of elevator cab 12 being equipped with an AED (Automated or semiautomatic External Defibrillator) 14 for purposes of illustration. As will be described, an elevator control unit that controls operation of elevator cab 12 receives input specifying an emergency medical situation, overrides regular operation of elevator cab 12, and directs elevator cab 12 to a floor of building 10 in response to the received input.

Building 10 comprises floors 16A–16H ("floors 16") and an elevator system that includes elevator cab 12, a hoistway 18, and a machine room 20. In the example of FIG. 1, elevator cab 12 services all floors 16. Machines within machine room 20 may move elevator cab 12 along hoistway 18. In the example illustrated in FIG. 1, machine room 20 is located over hoistway 18, such as on a roof of building 10. However, machine room 20 may be located elsewhere throughout building 10. Although the example of FIG. 1 illustrates floors 16A–16H, building 10 may include any number of floors 16. Elevator cab 12 may be a hydraulic elevator cab or a traction elevator cab. In addition, elevator cab 12 may be a passenger elevator cab or a service elevator cab.

In accordance with the invention, elevator cab 12 is equipped with an emergency medical device, such as AED 14. For example, a station mounted within elevator cab 12 may house AED 14. Elevator cab 12 may be directed to one of floors 16 in response to an emergency medical situation. More particularly, elevator cab 12 delivers AED 14 to a floor 16 on which the emergency medical situation occurs. For example, elevator cab 12 may deliver AED 14 to a floor 16 on which an individual suffers from cardiac arrest. The elevator cab 12 may further be directed to a floor on which a person trained to use AED 14 is located before being directed to floor 16 on which the emergency medical situation occurred. The trained person may be a security guard or other designated person for building 10. Delivering AED 14 to a location of an emergency medical situation allows the individual to receive therapy in advance of arrival of emergency personnel, which can save an individual's life.

Figure 2:
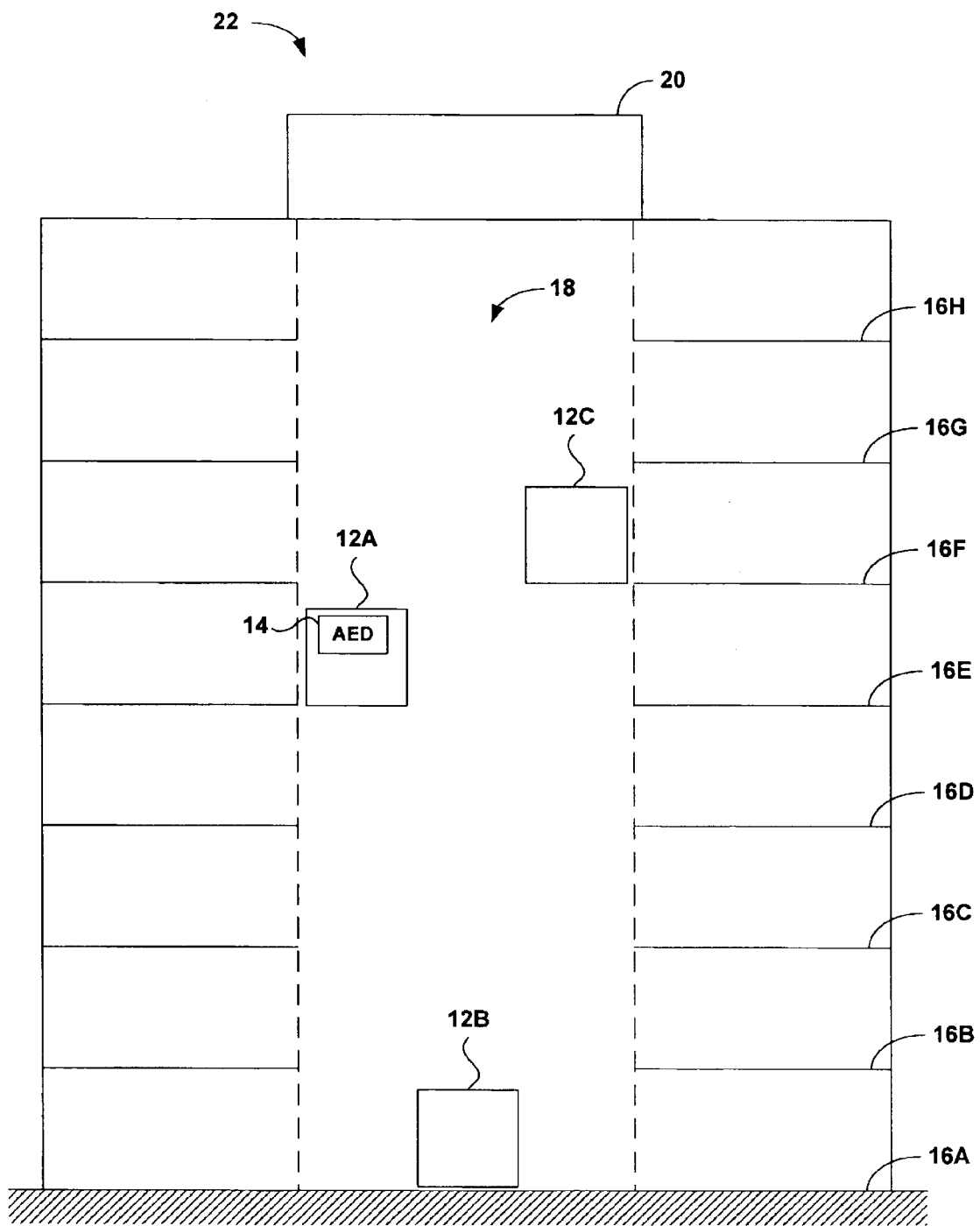
FIG. 2 is a diagram illustrating another building that includes a plurality of elevator cabs, at least one of which is equipped with an emergency medical device.

FIG. 2 is a diagram illustrating another building 22 that includes elevator cabs 12A–12C ("elevator cabs 12"), at least one of which is equipped with an emergency medical device. As with the example in FIG. 1, the invention will be described in context of elevator cab 12A being equipped with an automated external defibrillator (AED) 14 for purposes of illustration.

Building 22 comprises floors 16A–16H ("floors 16") and an elevator system that includes elevator cabs 12, a hoistway 18, and a machine room 20. As described above with respect to FIG. 1, machines within machine room 20 may move elevator cabs 12 along hoistway 18 to service floors 16. Machine room 20 may be located on a roof of building 10 or on any one of floors 16 within building 22. Although the example of FIG. 2 illustrates floors 16A–16H, building 22 may include any number of floors 16. In some embodiments, building 22 may include more than one hoistway 18. In that case, building 22 may include a machine room corresponding to each of the hoistways.

Each of elevator cabs 12 may service all of floors 16. However, in some embodiments, each of elevator cabs 12 may only service a portion of floors 16. For example, elevator cab 12A may service floors 16D–16E, elevator cab 12B may service floors 16A–16C, and elevator cab 12C may service floors 16F–16H. In this manner, floors 16 are subdivided in groups, sometimes referred to as banks, each served by dedicated elevator cabs 12. Elevator cabs 12 may be configured to service floors 16 of building 22 in numerous different configurations. For instance, the dedicated floors serviced by each of elevator cabs 12 may overlap.

In operation, a control unit overrides regular operation of elevator cab 12A in response to detection of an emergency medical situation. In some instances, the control unit may override regular operation of each of elevator cabs 12. For instance, an emergency medical situation, such as a sudden cardiac arrest, may occur on floor 16G Because elevator cab 12A (the cab equipped with AED 14) does not regularly service floor 16G, the control unit overrides regular operation of elevator cab 12A in order to direct elevator cab 12A to floor 16G, i.e., the floor on which the emergency medical situation occurred. In addition, the control unit may further override regular operation of elevator cabs 12B and 12C and reconfigure the operation of elevator cabs 12B and 12C in order to service floors 16D–16E, which are normally serviced by elevator cab 12A.

Further, the elevator control unit may direct elevator cab 12A to a floor on which a person trained to use AED 14 is located before directing elevator cab 12A to floor 16 on which the emergency medical situation occurred. Alternatively, another one of elevator cabs 12 from the group, e.g., elevator cab 12B or 12C, may be dedicated to picking up the person trained to use AED 14. As with elevator cab 12A, elevator cab 12B or 12C dedicated to picking up the trained person may be directed by elevator control unit 36 to override regular operation and provide express service for the trained person. Delivering AED 14 to a location of an emergency medical situation allows the individual to receive therapy in advance of arrival of emergency personnel, which can save an individuals life. Although in the example illustrated in FIG. 2 only one of elevator cabs 12 is equipped with an AED 14, any number of elevator cabs 12 may be equipped with an AED 14.

Figure 3:
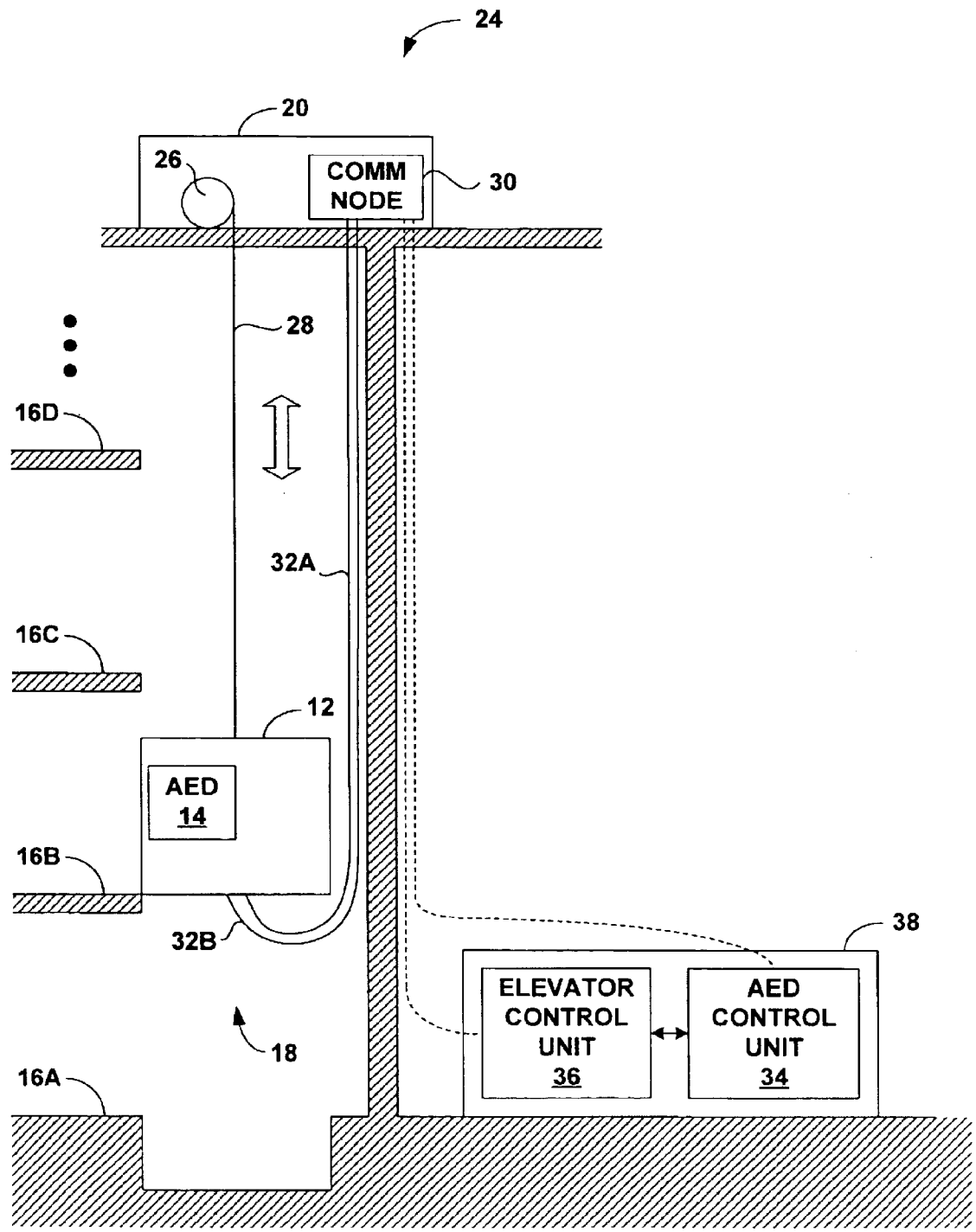
FIG. 3 is a diagram illustrating an elevator system of the building of FIG. 1 in further detail.

FIG. 3 is a diagram illustrating an elevator system 24 of building 10 of FIG. 1 in further detail. In accordance with the invention, elevator system 24 includes an elevator cab 12 equipped with an AED 14 that delivers AED 14 to a location of an emergency medical situation in response to receiving emergency medical input signifying an emergency medical situation.

Elevator cab 12 of the elevator system 24 depicted in FIG. 3 services floors 16A–16D ("floors 16"). As described above, elevator cab 12 travels up and down within a hoistway 18 to service floors 16. More particularly, at least one machine 26 within a machine room 20 moves elevator cab 12 along hoistway 18 to service floors 16. For example, a wire rope 28 may attach to a top of elevator cab 12 and machine 26 may retract wire rope 28 and extend wire rope 28 to raise and lower elevator cab 12 within hoistway 18, respectively. Machine room 20 may be located on a roof of building 10 as illustrated in FIG. 3. However, machine room 20 may be located on any one of floors 16 within the building, at a basement or the like.

Machine room 20 further includes a communication node (COMM NODE) 30. Traveling cables 32A and 32B ("traveling cables 32") extend from communication node 30 to elevator cab 12. Traveling cables 32 are used to transmit communications to elevator cab 12 and receive communications from elevator cab 12. Communication node 30 includes circuitry for driving and controlling communication. In the example illustrated in FIG. 3, traveling cables 32 attach to a bottom portion of elevator cab 12. However, traveling cables 32 may attach elsewhere to elevator cab 12, such as side of elevator cab 12 or a top portion of elevator cab 12.

Traveling cable 32A may be used for communication with AED 14. As illustrated in FIG. 3, an AED control unit 34 may communicate with AED 14 via traveling cable 32A. For example, AED control unit 34 and AED 14 may communicate with one another via traveling cable 32A for maintenance and testing purposes. In other words, AED control unit 34 may be used for testing the AED remotely, i.e., not by direct visual inspection. Alternatively, AED control unit 34 may communicate with a station (not shown) that houses AED 14 via traveling cable 32A. For example, upon removal of AED 14 from the station, the station may send a signal to AED control unit 34 via traveling cable 32A to indicate the removal of AED 14. The communications from AED 14 or the station housing AED 14 may be used to initiate contact with a safety agency, such as a monitoring service or an emergency services agency.

Traveling cable 32B also may be used for communication between an elevator push button panel within elevator cab 12 and an elevator control unit 36. Elevator control unit 36 may include at least one input medium and a display. Alternatively, elevator control unit 36 may include a display panel that is preferably located near a guard station of the building. An individual may actuate a button on the push button panel within elevator cab 12 to direct elevator cab 12 to a particular one of floors 16. In response to the actuation of the button, a signal may be sent to elevator control unit 36, which directs the elevator to the indicated floor 16.

Although in the example of FIG. 3 the elevator system generally includes traveling cables 32A and 32B for communication to and from the elevator, the elevator system preferably includes only a single traveling cable 32. For instance, the elevator system may have a single traveling cable 32. Cable 32 may includes at least one conductor dedicated to AED 14, while one or more other conductors are dedicated to other needs of elevator cab 12. Alternatively, AED 14 may use the traveling cable 32 by sharing a conductor with other needs of elevator cab 12. The conductors for AED 14 may carry power for maintaining a battery charged, communication signals as described elsewhere in this document, etc. Accordingly, AED 14 in elevator cab 12 may have its cables attached to traveling cables 32 at the bottom of elevator cab 12, and there is no need for separate wiring to support the incorporation of AED 14 in elevator cab 12, or to control travel of elevator cab 12 in response to a medical emergency. As described above, usually traveling cables 32 extend to a fixed point in the building, such as the middle of the hoistway. From there they may extend to the top of the hoistway and machine room 20, but that is not necessary.

Elevator system 24 delivers AED 14 to a floor on which an emergency medical situation occurs. More particularly, elevator control unit 36 receives input indicating an emergency medical situation, overrides regular operation of elevator cab 12, e.g., cancel active floor calls, and directs elevator cab 12 to one of floors 16 on which the emergency medical situation occurred. Elevator control unit 36 may receive input identifying the emergency medical situation from a user input medium. At least a portion of floors 16 may, for example, have user input media. Elevator cab 12 may also include a user input medium. The user input medium may comprise a switch, a button, a dial, a keypad or the like. The overriding of regular operation of elevator cab 12 and directing of elevator cab 12 to a floor of the emergency situation is distinct from overriding of regular operation for fire operation or for routine maintenance.

Elevator control unit 36 may further create a record of events responsive to receiving the emergency medical input. The record may, for example, include the time at which the emergency medical input was received, the floors elevator cab 12 traveled to responsive to the input, and the like.

An elevator management station 38 may contain elevator control unit 36 and AED control unit 34. Elevator management station 38 may, for example, be a guard station within building 10. Elevator management station 38 provides convenient access to elevator control unit 36 and AED control unit 34. For instance, an individual does not have to enter machine room 20 to access elevator control unit 36 and AED control unit 34. Elevator management station 38 may include one or more telephone lines. AED control unit 34 may, for example, use the telephone line for remote testing of AED 14. Alternatively, one or both of elevator control unit 36 and AED control unit 34 may be located remotely from building 10. For instance, a number of elevator companies at least monitor and possibly control a portion of the elevator cabs remotely using an elevator control unit 36 located at a facility owned by the elevator company, e.g., remote from building 10. In the same manner, an alarm monitoring service may monitor and communicate with AED 14 via an AED control unit 34 that is remote from building 10. In another example, a single remote location, such as the monitoring service may control operation of elevator system 24 in response to the emergency medical situation in addition to communications to AED 14. In other words, the monitoring service may include both AED control unit 34 and the elevator control unit 36.

AED control unit 34, elevator control unit 36 or both may operate according to executable instructions fetched from a computer-readable medium such as random access memory (RAM), read-only memory (ROM), non-volatile random access memory (NVRAM), electrically erasable programmable read-only memory (EEPROM), flash memory, and the like. The functions of AED control unit 34 or elevator control unit 36 may be implemented by executing the instructions of the computer-readable medium with one or more processors, discrete hardware circuitry, firmware, software executing on a programmable processor, or a combination of any of the above. These may be located within station 38, within the cab 12, communication node 30, machine room 20, other intermediate place, or be distributed between them. The flow diagrams of this document may well serve to implement these, alone or by imparting them into the otherwise regular features of the elevator system of the invention, such as the dispatch algorithms or other similar algorithms.

Figure 4:
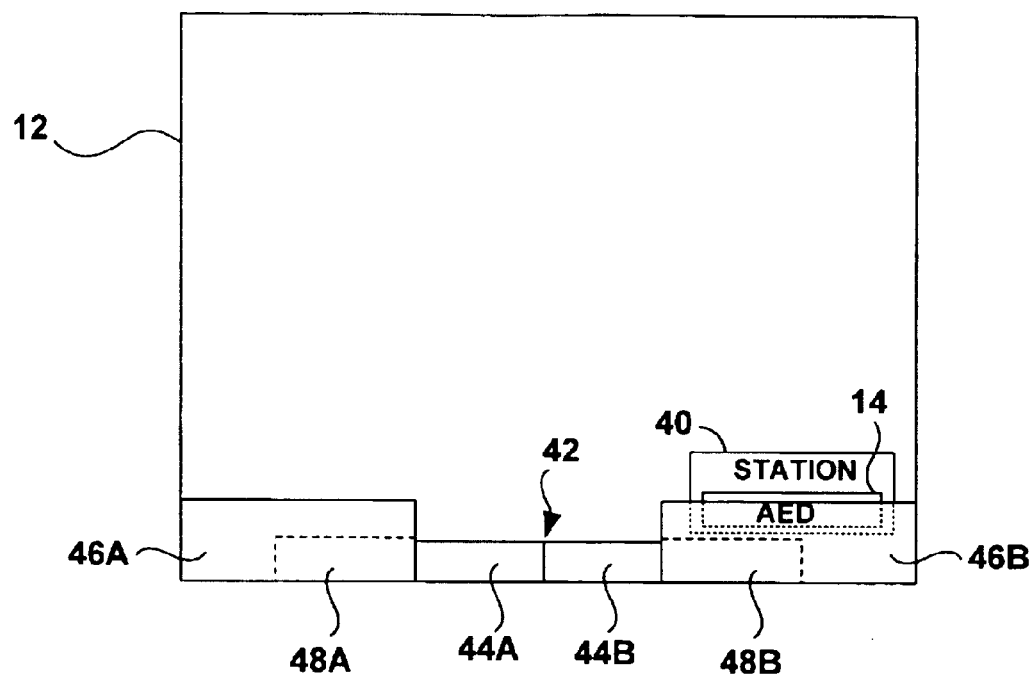
FIG. 4 is a top view of an exemplary elevator cab equipped with an automated external defibrillator (AED).

FIG. 4 is a top view of an exemplary elevator cab 12 equipped with an AED 14. As illustrated in the example of FIG. 4, AED 14 is housed within a station 40 that is recessed at least in part within one of front panels 48 of elevator cab 12. Elevator cab 12 includes an enclosure with an elevator door 42 that opens to allow passengers or items to enter and leave elevator cab 12. Elevator door 42 may include door sections 44A and 44B ("door sections 44"). When elevator cab 12 arrives at a desired floor 16, door sections 44A and 44B open by receding behind respective front panels 46A and 46B ("front panels 46"). Alternatively, elevator door 42 may be a single door section. In other words, elevator door 42 may open by receding behind a single front return 48

As described above, station 40 is recessed at least in part within one of front panels 46. Specifically, station 40 is at least in part between a main vertical surface of front panel 46B and the corresponding door section, when receded for opening. In this manner, the portion of station 40 between the main vertical surface of front panel 46B and return 48B does not interfere with opening of elevator door 42. Station 40 may be fully recessed within front panel 48. In other words, a door of station 40 may be substantially flush with the main vertical surface of front panel 48B. Elevator cab 12 may have a cutout to access AED 14 housed within station 40. Station 40 may be mounted in an opposite front panel 48 as a push button panel. Alternatively, push button panel and station 40 may be mounted on a same front panel 48. In this manner, elevator cab 12 is modified to house an AED station 40.

Figure 5:
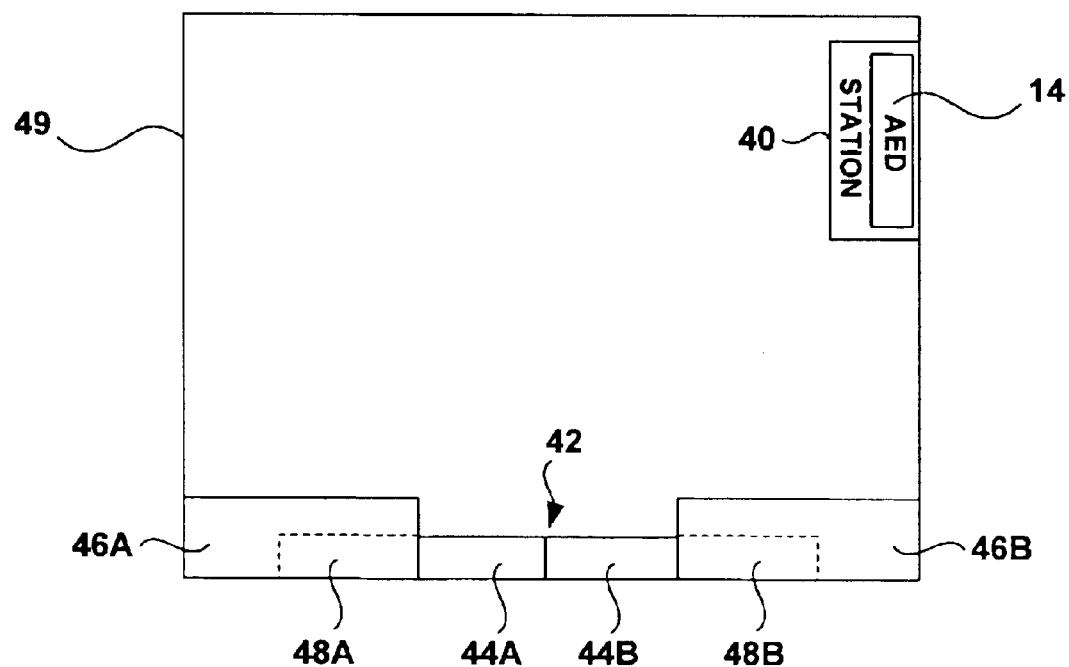
FIG. 5 is a top view of another exemplary elevator cab equipped with an AED.

FIG. 5 is a top view of another exemplary elevator cab 49 equipped with an AED 14. Elevator cab 49 conforms substantially to elevator cab 12 of FIG. 4, except that elevator cab 49 includes a station 40 to house AED 14 that is mounted on a wall adjacent elevator door 42. However, station 40 may be mounted on any wall of elevator cab 49. When station 40 is mounted on the wall, station 40 may be mounted at or above shoulder level in order to not interfere with passenger capacity of elevator cab 49, in the case in which elevator cab 49 is a passenger cab. Alternatively, station 40 may be partially or fully recessed within the wall of elevator cab 12.

Although in the example of FIG. 5 station 40 encloses AED 14, station 40 may be a mount on which AED 14 sits or a bracket from which AED 14 hangs. In either of these cases AED 14 may be exposed to the surrounding environment of elevator cab 49.

Figure 6:
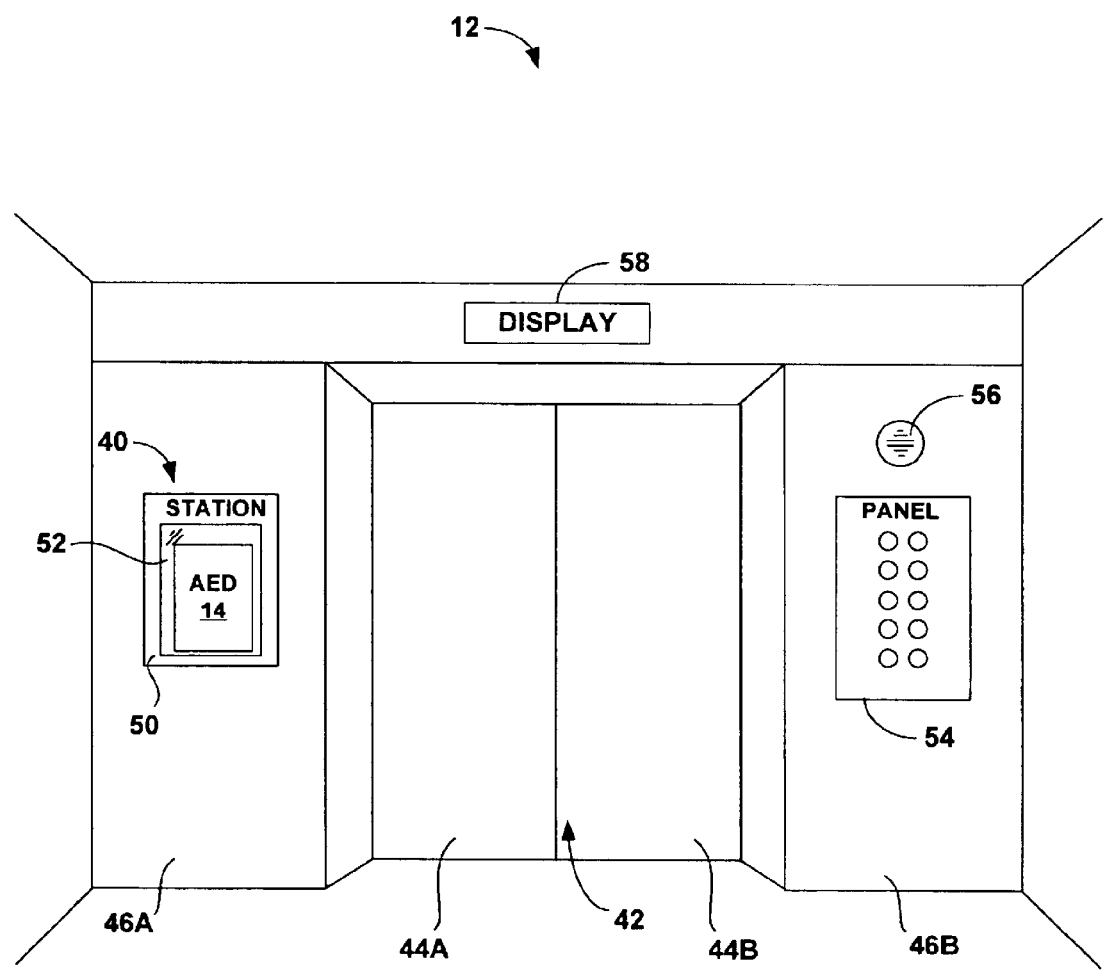
FIG. 6 is an elevation view from inside the elevator cab of FIG. 4, facing towards an elevator door of the elevator cab.

FIG. 6 is an elevation view from inside elevator cab 12 of FIG. 4, facing towards an elevator door 42 of elevator cab 12. In accordance with the invention, elevator cab 12 is equipped with an AED 14. More specifically, elevator cab 12 includes a station 40 that houses AED 14. As illustrated, station 40 and AED 14 may be located on or within a front panel 46 of elevator cab 12. In some embodiments, however, station 40 and AED 14 may be located on other walls of elevator cab 12.

As described above, elevator door 42 of elevator cab 12 may include door panels 44A and 44B ("door panels 44"). Each of door panels 44 may recede behind respective front panels 46. In some embodiments, elevator door 42 may be a single door panel that recedes behind one of the respective front panels 46.

In the example illustrated in FIG. 6, station 40 is at least partially recessed within front panel 46B. In other words, station 40 may be at least in part between a main vertical surface of front panel 46B. Station 40 may, for example, be fully recessed within front panel 48 such that a station door 50 is substantially flush with the main vertical surface of front panel 48B. Station 40, however, is mounted such that it does not recess far enough within front panel 46B to interfere with opening of elevator door 42.

Station door 50 encloses AED 14 to protect AED 14 from the surrounding environment of elevator cab 12. Station door 50 may include a translucent section 52 to allow visibility into station 40. In this manner, the contents of station 40 may be visible to an outside observer when station door 50 is closed. Translucent section 52 may be constructed of a translucent material such as a synthetic plastic, glass, or the like.

Elevator cab 12 further includes a push button panel 54. Push button panel 54 allows a passenger within elevator cab 12 to direct elevator cab 12 to a particular floor 16 serviced by elevator cab 12. Specifically, the passenger actuates a button on push button panel 54 associated with a particular floor 16. Push button panel 54 may communicate the input from the passenger, e.g., the actuation of the button, to elevator control unit 36. For example, push button panel 54 may communicate the input to elevator control unit 36 via one of traveling cables 32 (FIG. 3). In some embodiments, elevator control unit 36 may be located within elevator cab 12, e.g., within one of front panels 46 or within station 40.

Push button panel 54 may further include buttons for other elevator features such as an alarm or bell button, an emergency stop button, a button to hold elevator door 42 open, and the like. Push button panel 54 may further include other input media to receive input from passengers. For example, push button panel 54 may include switches, dials, keypads, or the like. A portion of the input media of push button panel 54 may be for use by authorized personnel only. Input media for authorized personnel only may need a key, a code, or other identifier in order to actuate the input media. For example, push button panel may include a key switch for maintenance operation, a key switch for fire operation, a key switch for emergency medical operation as per the invention.

Elevator cab 12 may further include a speaker 56, a display 58 or other output medium to communicate information to one or more passenger within elevator cab 12. The information output to the passengers may include location information of elevator cab 12, e.g. the current floor 16 on which elevator cab 12 is located, information apprising the passengers of the current situation, e.g., when regular operation is overridden because of an emergency medical situation, instructions on handling the emergency medical situation, e.g., commands to remove AED 14, exit elevator cab 12, and deliver AED 14 to medical personnel on site, or the like.

Although in the example illustrated in FIG. 6 station 40 housing AED 14 and push button control panel 54 are on opposite front panels 46, AED 14 and push button control panel 54 may be mounted on the same front panel 46. For example, station 40 and AED 14 may be may be located underneath push button control panel 54 on front panel 46A. Further, elevator cab 12 may have more than one push button panel 54, e.g., a push button control panel 54 located on each of front panels 46.

Figure 7:
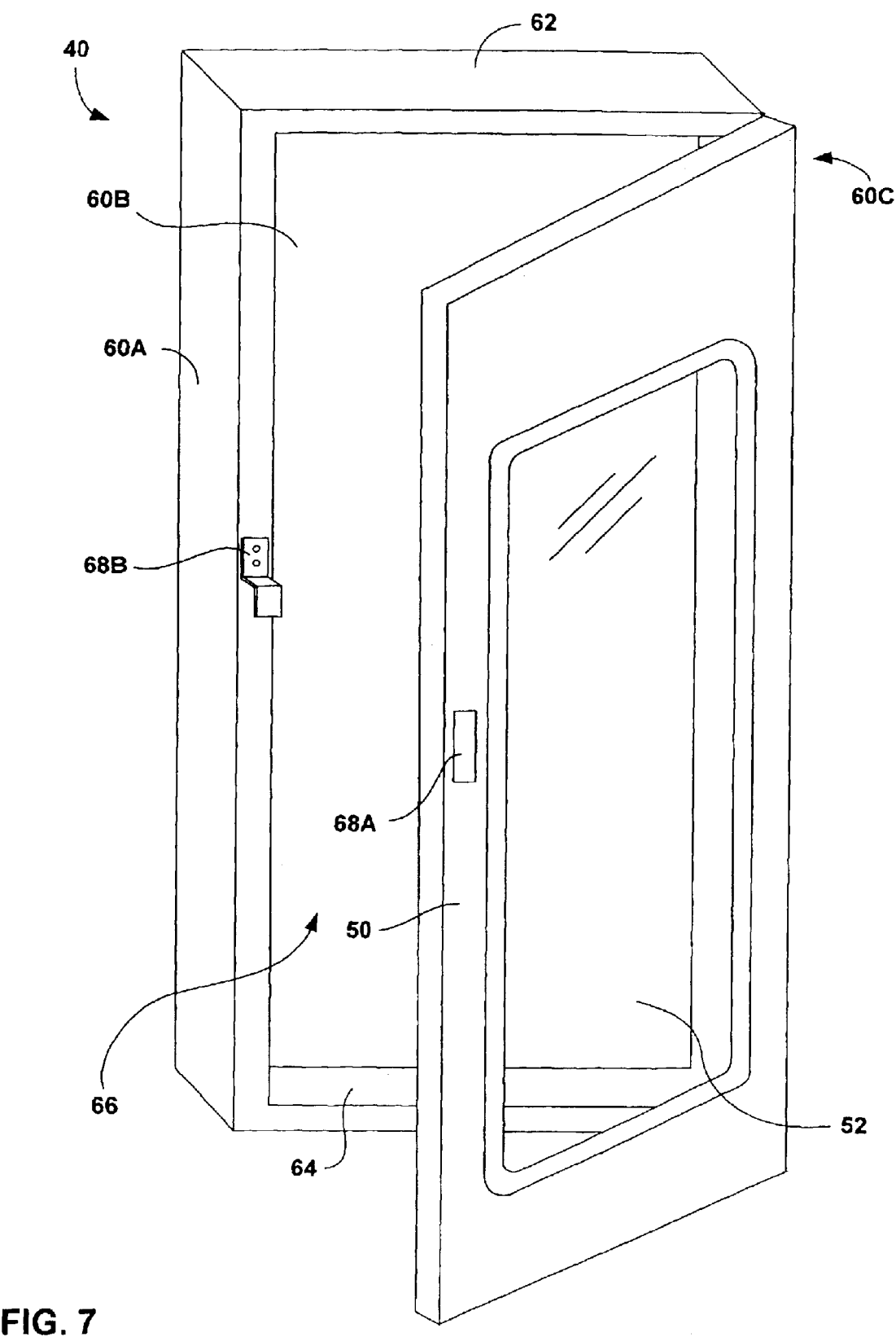
FIG. 7 is a block diagram of an exemplary station located within an elevator cab to house an emergency medical device.

FIG. 7 is a block diagram of an exemplary station 40 that may be located in elevator cab 12 to house an emergency medical device, such as AED 14. Station 40 comprises a plurality of wall sections 60A–60C ("wall sections 60"), a top section 62, and a bottom section 64 that define an interior compartment 66 of sufficient size to house AED 14. Station 40 may further include a station door 50 to enclose the medical device to protect the medical device from the surrounding environment of elevator cab 12. Station door 50 may include a translucent section 52 to allow visibility into interior compartment 66. In this manner, the contents of station 40 may be visible to an outside observer when station door 50 is closed yet be protected from incidental contact. Translucent section 52 may be constructed of a synthetic plastic, glass, or the like. Station 40, including wall sections 60, top section 62, bottom section 64, and station door 50 (not including translucent section 52), may be made from steel or other rigid, lightweight material.

Station 40 includes locking mechanisms 68A–68B ("68") to secure station door 50 in a closed position. Locking mechanism 68A is mounted on a wall section 60 of station 40 and locking mechanism 68B is mounted on station door 50. When station door 50 is closed, locking mechanism 68B receives locking mechanism 68A and secures station door 50 in the closed position. In order to open door 50, locking mechanism 68B may be pushed upward and door 50 may be pulled open. In some embodiments, a key may be needed to open locking mechanism 68. However, an individual may access AED 14 in an emergency by breaking translucent section 52.

Station 40 may include a retaining flange (not shown) that extends around station 40 to allow station 40 to be at least partially recessed into the wall. Recessing station 40 into the wall helps to minimize the amount of space required to accommodate station 40.

AED 14 stored in station 40 may be supported by bottom section 64. However, AED 14 may be stored within station 40 via any storage configuration. For example, AED 14 may be suspended from top portion 62 of station 40. Further, station 40 may include a mount to support AED 14. The mount may include, for example, a bracket connected to wall 60B of station 40 to support AED 14.

Station 40 may communicate with AED control unit 34 via one of traveling cables 32 (FIG. 3). Station 40 may send an indication to AED control unit 34 upon removal of AED 14. AED control unit 34 may also send communications to station 40. For example, AED control unit 34 may communicate with station 40 for AED maintenance purposes. Further, AED control unit 34 may signal station 40 to automatically unlock or open station door 50 in response to receiving input indicating an emergency medical situation.

Station 40 may include a detector (not shown) that detects the presence of AED 14. Detector 18 may be coupled to an alarm that activates upon detecting removal of the medical device from station 40. The alarm may be activated to alert people in the vicinity of the arrival of elevator cab 12 and, more particularly, AED 14. The detector may activate the alarm whether station door 50 of station 40 is opened or remains closed. The alarm may, for example, still activate when translucent section 52 is broken to remove AED 14 stored in station 40.

The detector may be implemented via various proximity sensors including a mechanical switch, a capacitive sensor, an emitter-detector circuit, a wireless detector, an optical detector, a receptacle plug sensor, or similar proximity sensor. The alarm may be a visual alarm such as a strobe light, an audible alarm such as a siren or a buzzer, or a combination visual and audible alarm.

Figure 8:
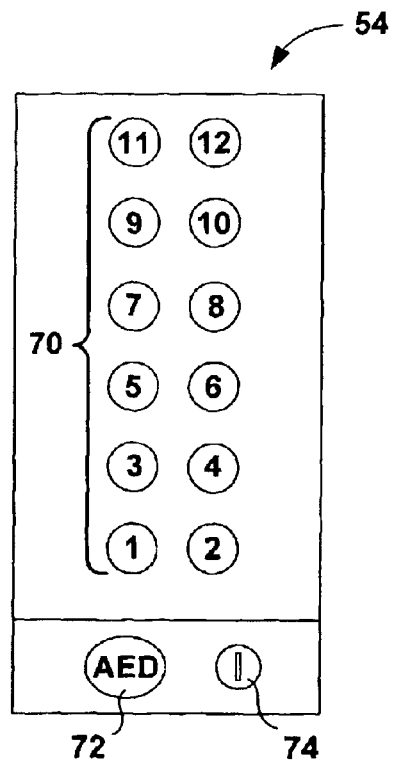
FIG. 8 is a schematic diagram illustrating an exemplary push button panel inside an elevator cab.

FIG. 8 is a schematic diagram illustrating an exemplary push button panel 54 inside an elevator cab 12. As described above, push button panel 54 includes riser floor buttons 70, which each correspond to a floor 16 of a building 10.

Push button panel 54 may further include an AED button 72 in addition to the standard portion push button portion. When actuated, AED button 72 transmits a signal to elevator control unit 30 indicating an emergency medical situation. Elevator control unit 30 overrides regular operation of elevator cab 12 in response to actuation of AED button 72. For example, actuating AED button 72 may cause elevator control unit 30 to cancel active floor calls. The passenger that actuated AED button 72 may then enter a floor 16 to direct elevator cab 12 to the floor on which the emergency medical situation occurred.

Push button panel 54 may further optionally include a switch, such as a key switch 74, that needs to be activated in order to actuate AED button 72. Key switch 74 may be keyed similar to fireman's operation, but adjusted for a paramedic, or other medically trained person. For instance, if key switch 74 were not activated, actuation of AED button 72 would not result in the override of regular operation of elevator cab 12. A guard at a guard station, a person trained to operate AED 14 or a paramedic may have a key to key switch 74. Alternatively, push button panel 54 may include a keypad where a code may be entered to initiate AED operation. The code is given only to those people in the building authorized to respond to medical incidents, and also outside trained personnel, etc.

Although not shown in FIG. 8, push button panel 54 may further include a key switch and button, similar to key switch 74 and button 72, to override regular elevator operation for different situations. For example, push button panel 54 may include and override key switch for a fire operation, for maintenance operation, or the like.

Figure 9:
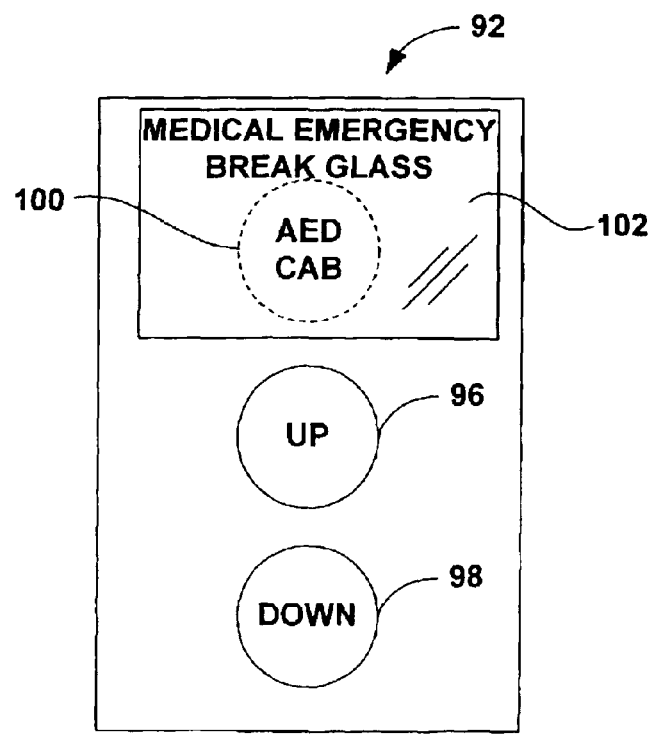
FIG. 9 is a schematic diagram illustrating an exemplary push button panel located on a floor of a building.

FIG. 9 is a schematic diagram illustrating a possible hall call station 92 according to the invention located on a floor 16 of a building. The hall call station 92 includes a push button panel with an "up" call button 96, a "down" call button 98, and an "AED cab" call button 100. As illustrated in the example of FIG. 9, AED cab call button 100 may be enclosed by a translucent cover 102 to protect the AED cab button from the surrounding environment. Hall call station 92 is ideally unique to the hoistway, whether one or more elevator cabs serve the floor of the associated hall call station 92. If a bank of more than two elevator cabs serves the particular floor, then the system of the invention dispatches the proper elevator cab to the floor.

An individual may actuate up call button 96 and down call button 98 to direct elevator cab 12 to floor 16 on which the individual actuated the respective call button. Up call button 96 and down call button 98 are used during standard operation of elevator cab 12.

However, actuation of AED cab call button 100, e.g., in the case of an emergency medical situation, immediately calls elevator cab 12 to the on which the hall call station 92 is located. This may be optionally implemented by canceling other floor calls.

In order to actuate AED cab call button 100, translucent cover 102 must be removed. Translucent cover 102 may, for example, may be broken in order to access and actuate AED cab call button 100. Alternatively, translucent cover 102 may be on a hinge and may be opened by an individual to access AED cab call button 100. Translucent cover 102 may be constructed of a translucent material such as a synthetic plastic, glass, or the like.

Figure 10:
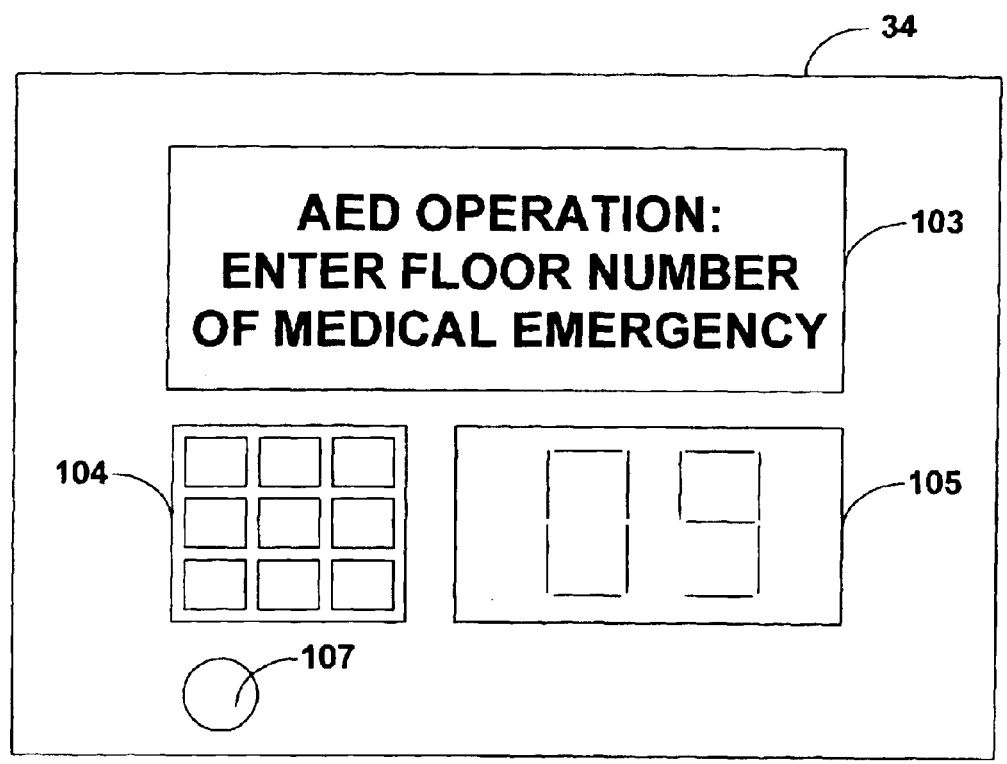
FIG. 10 is a block diagram illustrating an exemplary AED control panel located at an elevator management station as illustrated in FIG. 3.

FIG. 10 is a block diagram illustrating an exemplary AED control unit 34 located at elevator management station 38 as illustrated in FIG. 3. AED control unit 34 may include instructions 103. Instructions 103 may, for example read "AED OPERATION: ENTER FLOOR NUMBER OF MEDICAL EMERGENCY." AED control unit 34 may further include an input medium, such as keypad 104. An individual, such as a guard at a guard station, may input the floor number of the emergency medical situation using the input medium. AED control unit 34 also includes a display 105 to indicate the floor on which elevator cab 12 is currently located. In this manner, the individual at elevator management station 38 may track the location of elevator cab 12. AED control unit further includes an AED status indicator 107. AED status indicator 107 may, for example, be an LED that lights in response to receiving input identifying an emergency medical situation. In this manner, AED status indicator 107 indicates when elevator cab 12 is operating in AED operation mode.

In some embodiments, however, AED control unit 34 may be implemented in software, and its operation be through control screens. The software may be housed near a guard station as described above.

Upon receiving input identifying a floor of the emergency medical situation, AED control unit 34 relays the input to elevator control unit 36. In response to receiving the input, elevator control unit 36 overrides regular operation of elevator cab 12 and directs elevator cab 12 to the indicated floor on which the emergency medical situation occurred.

Figure 11:
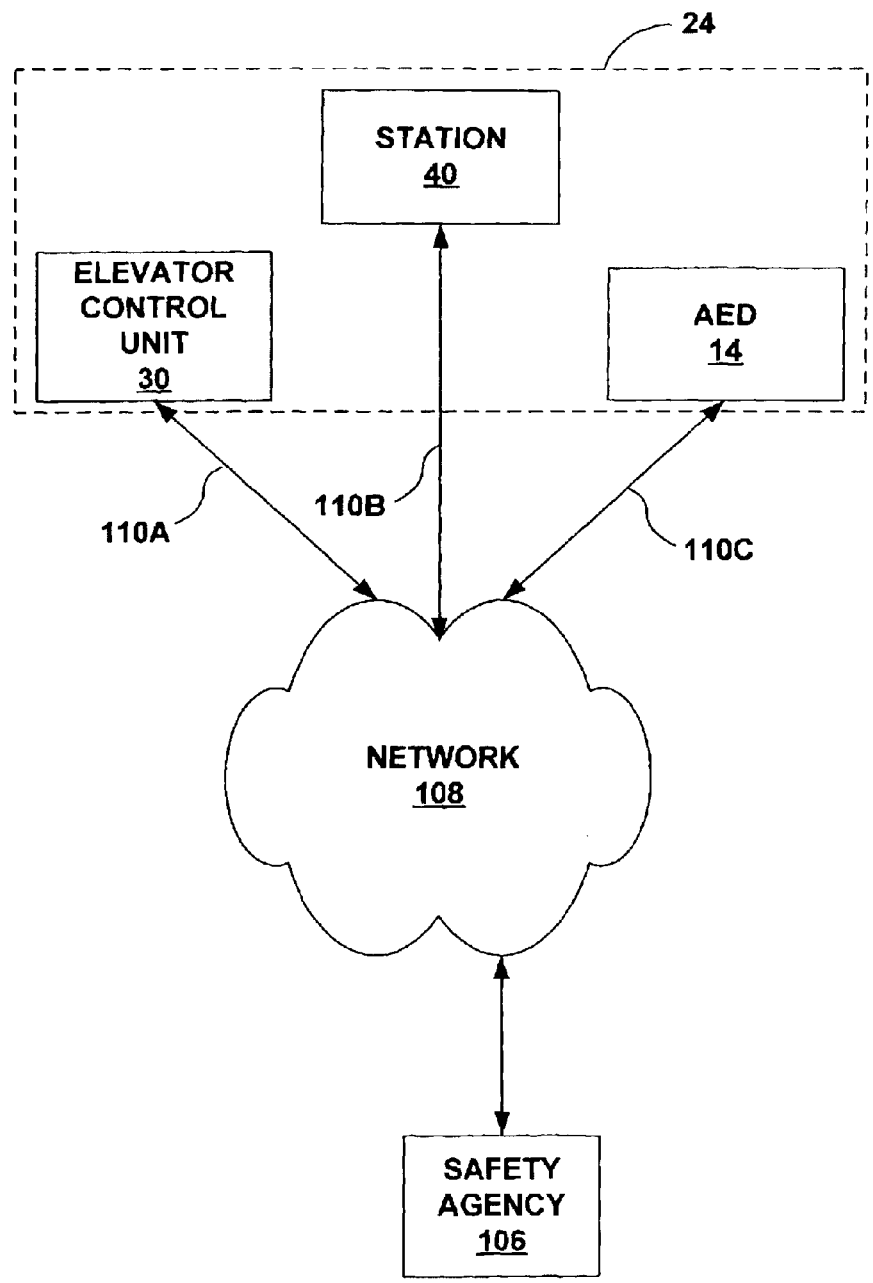
FIG. 11 is a block diagram illustrating an elevator system that provides direct communication with a safety agency in response to receiving emergency medical input signifying an emergency medical situation.

FIG. 11 is a block diagram illustrating an elevator system 24 that provides direct communication with a safety agency 106 in addition to directing an elevator cab 12 equipped with an AED 14 to a floor 16 on which an emergency medical situation occurs in response to receiving emergency medical input signifying a emergency medical situation. Direct communication between elevator system 24 and safety agency 106 may be initiated automatically upon receiving emergency medical input signifying the emergency medical situation, prompting early notification and arrival of emergency personnel. Safety agency 106 may be, for example, an Emergency Medical System such as 9-1-1 in the United States, or a security monitoring agency.

As shown in FIG. 11, direct communication with safety agency 106 may be initiated by station 40, by AED 14 or by elevator control unit 30. Each of the devices, e.g., station 40, AED 14 or elevator control unit 30, initiating direct communication may be coupled to a network 108 via links 110A–110C ("links 110"). More than one link 110 may couple station 40, AED 14 or elevator control unit 30 to network 108 in order to provide alternative communication paths between safety agency 106 and station 40, AED 14 or elevator control unit 30.

For example, station 40, AED 14 or elevator control unit 30 may include a communication unit such as a network card, a wireless local area network (WLAN) card, a mobile phone, an infrared (IR) card, a modem, or any combination thereof. Alternatively, station 40, AED 14 or elevator control unit 30 may couple to a communication device that is already coupled to network 108. For example, elevator control unit 30 may electrically couple to a mobile phone via a wireless or wired connection.

Network 108 may be a combination of network architectures, including a public switched telephone network (PSTN), an integrated services digital network (ISDN), an Internet protocol (IP) network, a local area network (LAN), a wide area network (WAN), a wireless communications network, or an asynchronous transfer mode (ATM) network. Links 110 may be wireless links, wired links, optical links or the like.

Station 40, AED 14 or elevator control unit 30 may, for example, send an advisory to safety agency 106 via communication unit 104A and network 108. In this manner, station 40 initiates direct communication between station 40 and safety agency 106. The communication may serve to request that emergency personnel be dispatched to the scene of the emergency. To that end, the communication may include location information, as well as other pertinent information. Direct communication between station 40 and safety agency 106 may advantageously reduce the amount of time before delivery of early advanced care to the patient.

Figure 12:
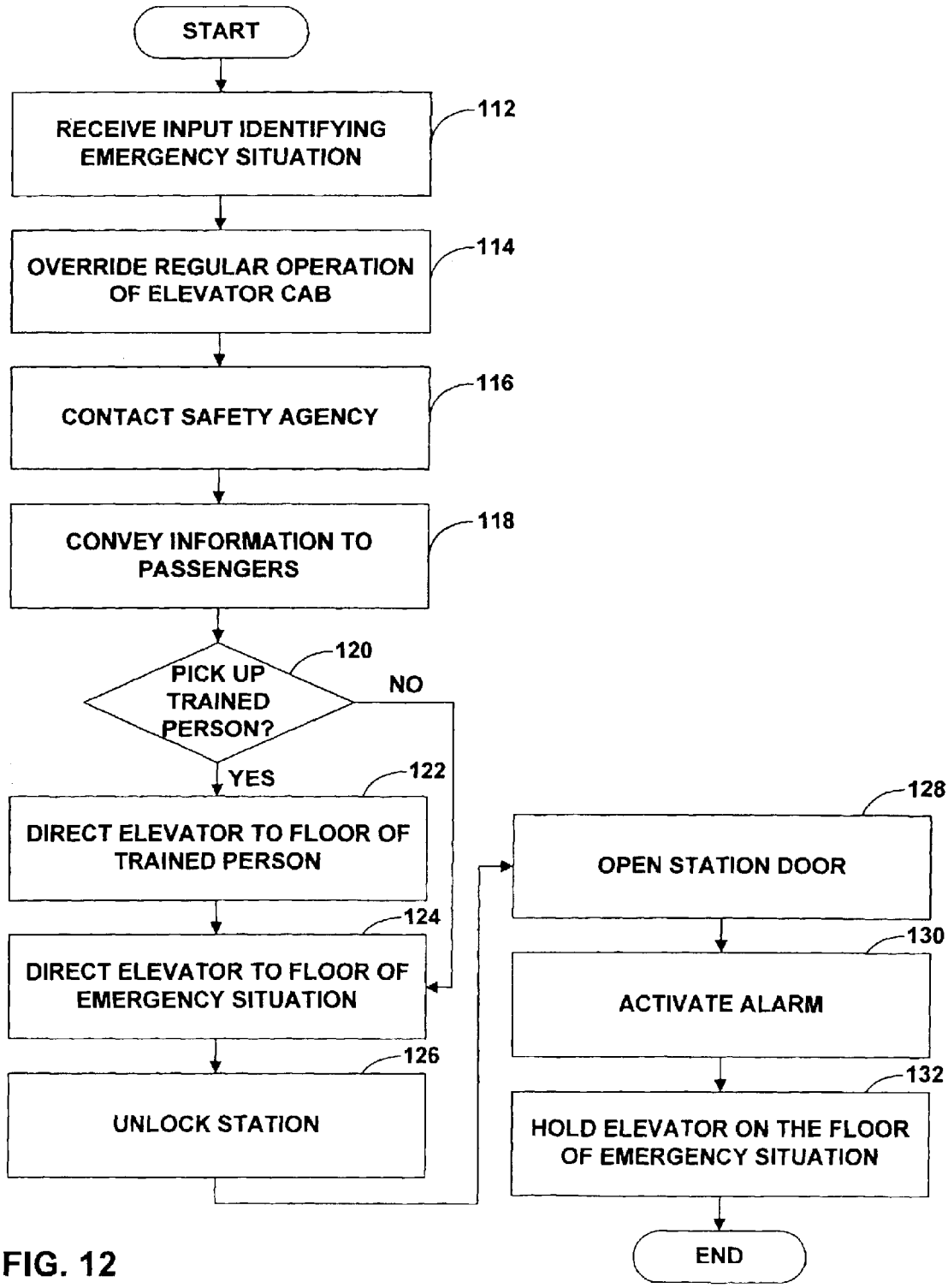
FIG. 12 is a flow diagram illustrating operation of elevator system that includes an elevator cab equipped with an AED in response to receiving emergency medical input signifying and emergency medical situation.

FIG. 12 is a flow diagram illustrating operation of elevator system 24 that includes an elevator cab 12 equipped with an AED 14. Initially, elevator control unit 36 receives emergency medical input signifying an emergency medical situation (112). Elevator control unit 36 may receive the emergency medical input via a user input medium such as a switch or button. For example, the user may actuate a button, such as AED button 100 of hall call station 92 (FIG. 9). In another example, the user may actuate an AED button 72 located on a push button panel 54 within elevator cab 12 as described in FIG. 8. In a further example, this input can be by a call from a bystander to a security guard, or a redirected call from a safety agency, such as a 9-1-1 emergency service, into the building. In response to the call a security guard or other individual may actuate the user input medium. The input may specify, for example, a floor 16 on which the emergency medical situation occurred.

Elevator control unit 36 overrides regular operation of elevator cab 12 in response to the input signifying an emergency medical situation (114). Elevator control unit 36 may, for example, cancel active floor calls of elevator cab 12. Further, if elevator cab 12 is part of a group of elevator cabs, elevator control unit 36 may first isolate the elevator cab carrying the medical device, and then reconfigure the operation of the remaining elevator cabs within the bank. Accordingly, elevator cab 12 stops operating as part of a group of elevators belonging in a bank, by being removed from group operation.

In addition, elevator system 24 may initiate contact with a safety agency 106 in response to the input signifying an emergency medical situation (116). For example, elevator control unit 36 may send an advisory to safety agency 106 to request that emergency personnel be dispatched to the scene of the emergency medical. The communication to safety agency 106 may include location information, as well as other pertinent information. Alternatively, AED 14 or station 40 may initiate contact with safety agency 106.

Further, elevator control unit 36 may convey information to passengers within elevator cab 12 in response to the input signifying an emergency medical situation (118). For instance, elevator control unit 36 may convey information to the passengers within elevator cab 12 via speaker 56 or display 58 as described in FIG. 6. The information conveyed to the passengers may include, for example, information apprising the passengers of the current situation, e.g., when regular operation is overridden because of an emergency medical situation. Additionally, instructions on handling the emergency medical situation, e.g., commands to remove AED 14, exit elevator cab 12, and deliver AED 14 to medical personnel on site may be conveyed to the passengers. For example, the passengers may be requested to exit the elevator cab, since it will most likely be used for continuing medical assistance.

Elevator control unit 36 may first determine whether to first pick up a person trained to use AED 14 (120), before going to the floor with the emergency. When elevator control unit 36 is configured to pick up a trained person, elevator control unit 36 directs elevator cab 12 to a floor 16 on which a person trained to use AED 14 is located (122). The trained person may be a security guard or other designated person for the building. After picking up the person trained to use AED 14 or if elevator control unit 36 is not configured to pick up a trained person, elevator control unit 36 directs elevator cab 12 to a floor 16 on which the emergency medical occurred (124). This is preferably an express service, e.g., elevator cab 12 goes directly to the indicated floors. When the elevator is traveling to the floor of the victim, the trained person may be preparing AED 14.

AED control unit 34 may automatically unlock door 50 of station 40 in response to a notification from elevator control unit 36 indicating that an emergency medical situation has occurred (126). For instance, AED control unit 34 may unlock door 50 as elevator cab 12 moves toward floor 16 on which the emergency medical situation occurred. In some embodiments, however, door 50 may not have a lock. Further, AED control unit 34 may automatically open door 50 of station 40 in response to a notification from elevator control unit 36 (128).

Elevator control system 24 activates an alarm (130). Elevator control system may, for example, activate the alarm to notify people in the vicinity that elevator cab 12 equipped with AED 14 has arrived so that people on the floor will go and take AED 14 from elevator cab 12. The alarm may be activated upon arrival of elevator cab 12 equipped with AED 14 at floor 16 on which the emergency medical situation occurred. Alternatively, the alarm may be activated upon removal of AED 14 from station 40.

Elevator control unit 36 may hold elevator cab 12 on floor 16 on which the emergency situation occurred (132). In this manner, elevator cab 12 will be immediately available to bring the victim to the ground floor to be moved to a hospital or other such location.

Figure 13:
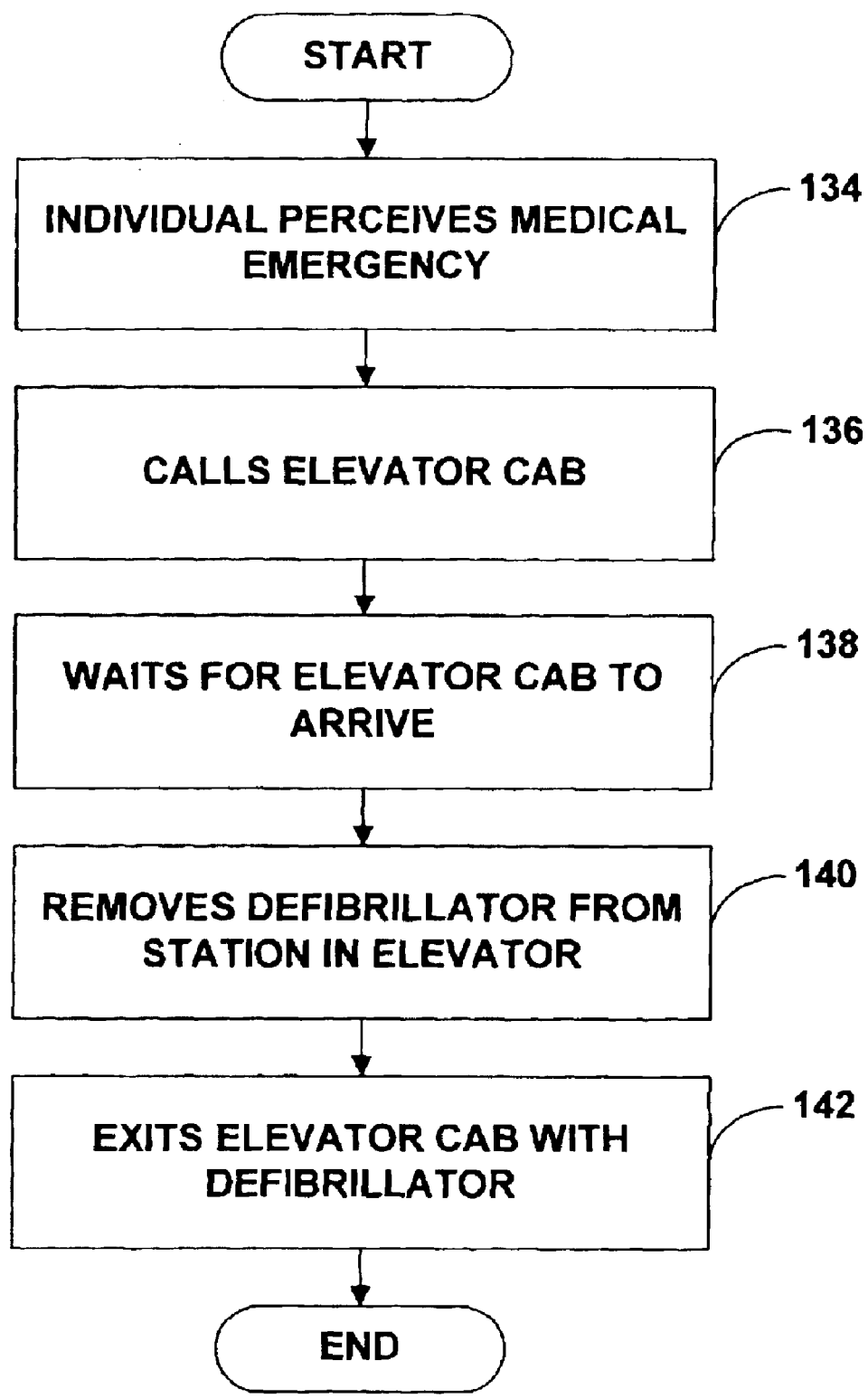
FIG. 13 is a flow diagram illustrating an exemplary response to an emergency medical situation in accordance with the invention.

FIG. 13 is a flow diagram illustrating an exemplary response to an emergency medical situation in accordance with the invention. Initially, an individual perceives an emergency medical situation (134). In response to perceiving the emergency medical situation, the individual calls an elevator cab 12 equipped with an emergency medical device, such as an AED 14 (136). The individual may call elevator cab 12 by actuating a button, such as AED button 100 of hall call station 92 illustrated in FIG. 9. As described above, a push button panel similar to hall call station 92 may be installed on each floor 16 of a building.

The individual waits for elevator cab 12 equipped with AED 14 to arrive (136). Upon arrival of elevator cab 12, the individual removes AED 14 from station 40 within elevator cab 12 (140) and exits elevator cab 12 with AED 14 (142).

Various embodiments of the invention have been described. These embodiments are illustrative of the practice of the invention. Various modifications may be made without departing from the scope of the claims. These and other embodiments are within the scope of the following claims.

What is claimed is:

1. A method comprising:
   receiving emergency medical input signifying an emergency medical situation at a floor of a building;
   overriding regular operation of an elevator cab that carries an emergency medical device in response to receiving the input; and
   directing the elevator cab to the floor.

2. The method of claim 1, in which overriding and directing is distinct from manual key switch override for fire operation and maintenance operation.

3. The method of claim 1, in which overriding operation of the elevator cab includes canceling active floor calls.

4. The method of claim 1, further comprising conveying information to a passenger within the elevator cab.

5. The method of claim 4, in which conveying information to the passenger includes conveying instructions.

6. The method of claim 1, further comprising directing the elevator cab to a floor on which a person trained to use the emergency medical device is located.

7. The method of claim 1, in which receiving input is performed via a user input medium.

8. The method of claim 7, in which the user input medium is on the floor on which the emergency situation occurs.

9. The method of claim 8, in which the user input medium is enclosed by at least one piece of glass and a user breaks the piece of glass to access the switch.

10. The method of claim 7, in which the user input medium is located within the elevator cab.

11. The method of claim 7, in which the user input medium is activated by a key.

12. The method of claim 7, in which the user input medium comprises one of a switch, a button, a dial, and a keypad.

13. The method of claim 1, further comprising automatically unlocking a station that houses the emergency medical device in response to receiving the input.

14. The method of claim 1, further comprising automatically opening a door of a station that houses the emergency medical device in response to receiving the input.

15. The method of claim 1, further comprising activating an alarm upon removal of the emergency medical device from the station.

16. The method of claim 1, further comprising activating an alarm upon arrival of the elevator cab at the floor on which the emergency situation occurs.

17. The method of claim 1, further comprising contacting a safety agency.

18. The method of claim 17, in which contacting the safety agency includes sending an advisory to the safety agency.

19. The method of claim 18, in which the advisory includes at least one of location information, contact information of a prescribing physician, and a serial number of the emergency medical device.

20. The method of claim 1, further comprising creating a record of events responsive to receiving the input.

21. The method of claim 20, further comprising adding to the record the floors the cab traveled to responsive to receiving the input.

22. The method of claim 1, in which the emergency medical device includes an automated external defibrillator.

23. A system comprising:
an elevator cab moveable within a building;
a traveling cable attached to the bottom of the cab and to a fixed point of the building; and
a defibrillator in a station of the cab that communicates via the traveling cable.

24. The system of claim 23, in which the traveling cable includes at least one conductor dedicated for the defibrillator.

25. The system of claim 23, in which the traveling cable includes at least one conductor dedicated for the station.

26. The system of claim 23, in which the traveling cable includes at least one conductor that is shared for communication by the defibrillator and another feature of the cab.

27. The system of claim 23, in which the defibrillator communicates via the traveling cable for maintenance purposes.

28. The system of claim 23, further comprising an elevator control unit to control the operation of the elevator cab, the elevator control unit receiving input identifying an emergency medical situation, overriding operation of the elevator cab, and directing the elevator cab to a floor of the building on which the emergency situation occurs in response to the received input.

29. The system of claim 28, in which overriding and directing is distinct from manual key switch override for fire operation and maintenance operation.

30. The system of claim 28, in which the control unit further directs the elevator cab to a floor to on which a person trained to use the defibrillator is located.

31. The system of claim 28, further comprising an input medium to notify the control unit of the emergency situation.

32. The system of claim 23, further comprising an alarm to indicate arrival of the defibrillator.

33. An elevator cab comprising:
an enclosure with an openable elevator door;
a front panel behind which the door recedes for opening; and
a defibrillator in a station, wherein the station is at least in part between a main vertical surface of the front panel and the door when receded.

34. The cab of claim 33, in which the front panel has a cutout to access the defibrillator in the station.

35. The cab of claim 33, further comprising a traveling cable attached to the bottom of the enclosure, in which the station is adapted to communicate via the traveling cable.

36. The cab of claim 35, in which the defibrillator communicates via the traveling cable for maintenance purposes.

37. The cab of claim 35, in which the station communicates with a safety agency via the traveling cable.

38. The cab of claim 37, in which the station communicates with a safety agency via the traveling cable in response to detecting removal of the defibrillator from the station.

39. The cab of claim 33, in which the station activates an alarm in response to detecting removal of the defibrillator from the station.

40. A system comprising:
an elevator cab in a building;
a station within the elevator cab that houses an emergency medical device; and
an elevator control unit to control the operation of the elevator cab, the elevator control unit receiving input identifying an emergency situation, overriding regular operation of the elevator cab, and directing the elevator cab to a floor of the building on which the emergency situation occurs in response to the received input.

41. The system of claim 40, in which overriding and directing is distinct from manual key switch override for fire operation and maintenance operation.

42. The system of claim 40, in which the control unit further directs the elevator cab to a floor on which a person trained to use the emergency medical device is located.

43. The system of claim 40, further comprising an input medium to notify the control unit of the emergency situation.

44. The system of claim 43, in which the input medium is located within the elevator cab.

45. The system of claim 43, in which a key activates the input medium.

46. The system of claim 43, in which the input medium comprises a plurality of input media located at floors of the building.

47. The system of claim 43, in which the input medium includes one of a switch, a button, a dial, and a keypad.

48. The system of claim 40, in which the elevator cab is one of a plurality of elevator cabs, and the elevator control unit independently controls operation of the elevator cab in response to the input identifying the emergency situation.

49. The system of claim 40, in which the elevator control unit is located within the elevator cab.

50. The system of claim 40, in which the elevator control unit is located within a machine room associated with the cab.

51. The system of claim 40, further comprising an alarm to indicate arrival of the emergency medical device.

52. The system of claim 51, in which the alarm is activated upon removal of the emergency medical device from a station in which the device is stored.

53. The system of claim 51, in which the alarm is activated upon the elevator cab arriving at the floor on which the emergency situation occurs.

54. The system of claim 40, further comprising a station mounted within the elevator cab in which the emergency medical device is housed.

55. The system of claim 54, in which the station includes a locking mechanism to lock the station.

56. The system of claim 55, in which the station automatically unlocks the locking mechanism in response to the input identifying the emergency situation.

57. The system of claim 54, in which a door of the station automatically opens in response to the input identifying the emergency situation.

58. The system of claim 40, in which the elevator cab further includes an output medium to convey a message to one or more passengers of the elevator cab.

59. The system of claim 58, in which the output medium includes at least one of a display and a speaker.

60. The system of claim 40, further comprising a traveling cable attached to the bottom of the elevator cab from the outside to transmit communication signals.

61. The system of claim 60, in which the traveling cable includes at least one conductor dedicated for the emergency medical device.

62. The system of claim 60, the emergency medical device communicates via the traveling cable for maintenance purposes.

63. The system of claim 40, in which the emergency medical device includes an automated external defibrillator.

64. The system of claim 40, in which the elevator cab is a passenger elevator cab.

65. A computer-readable medium comprising instructions to cause a processor to:

receive a emergency medical input signifying a emergency medical situation;

override regular operation of an elevator cab that carries an emergency medical device suitable for the situation in response to receiving the input; and direct the elevator cab to a floor on which the emergency situation occurs.

66. The computer-readable medium of claim 65, in which instructions that cause the processor to override operation of the elevator cab include instructions to cause the processor to cancel active floor calls.

67. The computer-readable medium of claim 65, further comprising instructions to cause the processor to convey information to a passenger within the elevator cab.

68. The computer-readable medium of claim 65, further comprising instructions to cause the processor to direct the elevator cab to a floor on which a person trained to use the emergency medical device is located.

69. The computer-readable medium of claim 65, further comprising instructions to cause the processor to:

identify one elevator cab of a group that includes a defibrillator, and remove the identified cab from group operation.

* * * * *